United States Patent
Derrieu et al.

(10) Patent No.: US 9,131,689 B2
(45) Date of Patent: Sep. 15, 2015

(54) USE OF A 1-N-(HALO-3-PYRIDYLMETHYL)-N-METHYLAMINO-1-ALKYLAMINO-2-NITROETHYLENE DERIVATIVE FOR PREPARING A TOPICAL VETERINARY PHARMACEUTICAL COMPOSITION FOR COMBATING EXTERNAL PARASITES

(71) Applicant: VIRBAC, Carros (FR)

(72) Inventors: Guy Derrieu, Cagnes sur Mer (FR); Jean Pascal Marc, Saint Paul (FR)

(73) Assignee: Virbac, Carros (FR)

( * ) Notice: Subject to any disclaimer, the term of this patent is extended or adjusted under 35 U.S.C. 154(b) by 63 days.

(21) Appl. No.: 13/691,141

(22) Filed: Nov. 30, 2012

(65) Prior Publication Data

US 2013/0096164 A1      Apr. 18, 2013

Related U.S. Application Data

(62) Division of application No. 12/682,133, filed as application No. PCT/FR2008/001423 on Oct. 10, 2008.

(30) Foreign Application Priority Data

Oct. 11, 2007 (FR) .................................. 07 07127

(51) Int. Cl.
*A61K 31/415* (2006.01)
*A61K 31/44* (2006.01)
*A01N 43/40* (2006.01)

(52) U.S. Cl.
CPC ............... *A01N 43/40* (2013.01); *A61K 31/415* (2013.01); *A61K 31/44* (2013.01)

(58) Field of Classification Search
CPC ... A01N 2300/00; A01N 25/00; A01N 43/40; A01K 27/007; A61K 31/415; A61K 31/44
See application file for complete search history.

(56) References Cited

FOREIGN PATENT DOCUMENTS

| | | |
|---|---|---|
| DE | 198 07 633 A1 | 8/1999 |
| EP | 0 976 328 A2 | 2/2000 |
| EP | 1 668 984 A1 | 6/2006 |
| GB | 2 321 012 A | 7/1998 |
| JP | 2003-26603 A | 1/2003 |
| JP | 2003-95813 A | 4/2003 |
| WO | WO-93/24002 A1 | 12/1993 |
| WO | WO-00/29378 A2 | 5/2000 |
| WO | WO-2004/064522 A1 | 8/2004 |
| WO | WO-2004/089239 A2 | 10/2004 |

OTHER PUBLICATIONS

The International Search Report for PCT/FR2008/001423, mailed Oct. 20, 2009.
Bulletin Officiel n°2003-21, "Avis relative a l'octroi d'autorisations de mise sur le marche de medicaments veterinaires," Ministry of Health—France, Apr. 28, 2008, <http://www.sante.gouv.fr/adm/dagpb/bo/2003/03-21/a0211447.htm>.
Frontline Top Spot for Dogs 1996; Package Label and Dosage Micropippette Carrier.

*Primary Examiner* — Aradhana Sasan
(74) *Attorney, Agent, or Firm* — Alston & Bird LLP (57) ABSTRACT

The present invention relates to the use, as active ingredient, of a 1-N-(halo-3-pyridylmethyl)-N-methylamino-1-alkylamino-2-nitroethylene derivative for preparing a veterinary pharmaceutical composition for topical application in the treatment of external parasites, in particular fleas, in domestic animals, in particular in dogs and cats, intended to be applied at least every 2 weeks.

25 Claims, 3 Drawing Sheets

USE OF A 1-N-(HALO-3-PYRIDYLMETHYL)-N-METHYLAMINO-1-ALKYLAMINO-2-NITROETHYLENE DERIVATIVE FOR PREPARING A TOPICAL VETERINARY PHARMACEUTICAL COMPOSITION FOR COMBATING EXTERNAL PARASITES

FIELD OF THE INVENTION

The present invention relates to the use, as active ingredient, of a 1-N-(halo-3-pyridylmethyl)-N-methylamino-1-alkylamino-2-nitroethylene derivative for preparing a veterinary pharmaceutical composition for topical application in the treatment of infestations with external parasites, in particular fleas, in domestic animals, in particular in dogs and cats.

BACKGROUND OF THE INVENTION

The infestation of domestic animals with blood-feeding parasites, in particular with ticks and fleas, is a considerable health problem.

Fleas are wingless insects which have a laterally compressed body and highly developed legs suitable for jumping. They are blood-sucking ectoparasites of mammals or birds. The some 2000 species listed belong to the order Siphonaptera.

Two species of fleas are commonly encountered in Europe; they are the cat flea (*Ctenocephalides felis*) and the dog flea (*Ctenocephalides canis*) which live in the fur of the animals. The cat flea, which is the most common, is capable or reproducing on both cats and dogs. It can also attack humans and other pets; however, the cat is the main animal responsible for infestation when cats and dogs live in the same environment.

Fleas have a complex life cycle with 4 distinct stages: egg, larva, pupa and adult. They mate in the first 8 to 48 hours following acquisition by the host, after their first blood meal. The females thus begin to lay eggs 24 to 48 hours after this first blood meal. The adult flea generally lays eggs on the animal. The eggs laid on the animal do not however remain there, and fall to the ground. Under optimum conditions, the female can lay more than 25 eggs a day. She will lay several hundred eggs throughout her life. After a few days, a hairy white wormlike larva, approximately 1.5 mm long, is born. The larva feeds on organic debris, on larval remains and on dry blood defecated by the adults. The larval state lasts 1 to 3 weeks, if conditions are favorable (18° C. to 27° C. and 70% relative humidity). The larva then spins a cocoon and pupates. Normally, the pupa evolves in 1 to 2 weeks, but passage to the adult state can extend up to one year, if conditions are unfavorable. The adult flea (small and black) emerges from the cocoon when it detects vibrations, heat, or a higher concentration of carbon dioxide, which occurs when a cat, a dog . . . or a human! passes by. It then jumps onto the victim, immediately feeds on blood and rapidly grows, becoming a lighter, reddish-brown color. The adult flea lives for 6 to 12 months. It can survive for up to 2 months without food.

Flea bites cause itching in both animals and humans. The flea saliva (secreted at each bite) can also, depending on individuals, lead to immediate or delayed allergic reactions. These reactions result in various skin lesions and itching. Two types of flea-related dermatosis are distinguished: namely pulicosis and flea allergy dermatitis. While in both cases the dermatosis results from a more or less substantial infestation with fleas, only in the second case is there an associated allergic phenomenon. Flea allergy dermatitis (FAD) is the most common cause of pruritus in dogs. In France, in adult dogs, it thus represents close to half the pruritic dermatoses. Close to 80% of dogs which exhibit FAD also have atopic dermatitis, and, vice versa, two atopic dogs out of three exhibit FAD. It is therefore probable that atopic dogs are predisposed to the development of a flea allergy and that infestation with the latter is a triggering factor for atopic dermatitis. This is proof of the need for a very intensive antiflea control in atopic dogs or dogs belonging to breeds at risk. Furthermore, FAD is probably the main cause of the reappearance of pruritus in desensitized atopic dogs.

Fleas of the *Ctenocephalides* genus are, moreover, intermediate hosts of *Dipylidium caninum*, which is a parasitic worm of the small intestine of dogs and cats. The carnivore becomes infested by swallowing the parasitized fleas. This infestation can cause anal pruritis, engorgement of the anal sacs, and also dermatitis of the perineal region. It is therefore sometimes recommended to worm animals regularly in addition to combating fleas.

Flea infestations therefore represent a considerable problem for the animals which are infested and make it necessary to have suitable treatments. It is in particular advisable for the treatment to have not only an immediate efficacy (rapidity of action), but also an efficacy sustained over time (persistence) in order to avoid, on the one hand, repeat treatments and, on the other hand, any risk of infestation and/or reinfestation for a sustained period. The flea must be eliminated before it reproduces and begins to lay eggs.

There are currently various types of insecticidal treatments against fleas on the market (shampoos, powders, aerosols, collars, tablets, liquid compositions for topical application). However, not all these treatments always give complete satisfaction.

Antiparasitic shampoos constitute a good "attack treatment" in the case of massive infestations, but do not have a long-lasting effect. They treat only the adult fleas and are particularly difficult to use on cats, which do not generally appreciate baths.

Antiparasitic powders contain an insecticidal active ingredient diluted in talc. This method of application is not very effective since the talc slides along the coat and the product rarely penetrates as far as the skin. Furthermore, there is a risk that the animals will accidentally ingest the insecticidal active ingredient or the other constituents of the composition when they lick themselves. The use of powder is also not very convenient, since the application thereof can take several minutes, may not be uniform over all the animal's fur and is accompanied by pulverulent particles being given off and being inevitably inhaled by the animal and its owner even in the case of particularly meticulous application.

This type of problem is also encountered with the use of mechanical vaporizers or sprays, or of aerosols (for example, based on permethrin as active ingredient) which, furthermore, have the additional drawback of generating stress or an aggressive reaction in the animal to which it is applied, given the noise generated at the time of spraying. The compositions applied by virtue of these devices are, moreover, generally not very persistent (maximum of 1 week) and poorly water resistant.

Antiflea collars are generally quite effective in a temporary manner. However, their efficacy is essentially limited to the regions of the animal which are close to the collar (neck, nose, thorax). On the other hand, on the other parts of the animal, the efficiency of antiflea collars can be very poor, or even nonexistent. Furthermore, cats which are used to going out risk getting their collar caught on a branch or wire fencing and of hurting themselves by becoming strangled.

The systemic, in particular oral or parenteral, administration of pharmaceutical compositions already represents a certain advance, in terms of efficiency, compared with the various treatments detailed above. Quite a wide choice of preparations using various active ingredients known to have an antiflea activity is currently found on the market. In the event of an oral administration, these active ingredients are absorbed at the gastrointestinal level and find their way to the animal's blood so as to cause poisoning of the fleas during the bite. Among products of this type, mention may in particular be made of the product Capstar®, using, as active ingredient, nitenpyram (the chemical name of which is (E)-N-(6-chloro-3-pyridylmethyl)-N-ethyl-N'-methyl-2-nitrovinylidenediamine according to the IUPAC nomenclature), as described, for example, in patent application EP 0 616 494. The Capstar® product, which is in the form of tablets for dogs and cats, has a highly rapid action. Specifically, the maximum blood concentration is reached in 30 to 120 minutes in fasting dogs and cats. However, the plasma half-life of the active ingredient is 4 hours in dogs and 8 hours in cats; 90% of the molecule being secreted in the urine in one day in dogs and in two days in cats. Thus, this product is effective for a very short period of time and it is necessary to administer it daily according to the producer's recommendations. This product also has the drawback of being in the form of tablets, the administration of which is not easy, or is even impossible, in certain relatively uncooperative, or particularly ferocious, animals.

Finally, the marketed products that are active against fleas can also be in the form of liquid compositions (pipettes) or "spot-on" solutions for the skin, that are applied very easily, in one go, topically, directly to the animal's skin, generally between the shoulder blades. By way of examples of products of this type, mention may be made of:

fipronil-based products, such as the product Frontline® Spot-On Chat et Chien, sold in France by the company Merial SAS. It is often presented as a product of choice for preventing and treating flea infestations. However, according to the producer's data, the fipronil active concentration threshold is exceeded after 24 hours over the entire body surface of the animal and it therefore has the drawback of not being very rapidly active. Moreover, the period of protection against further infestations is limited to 4 weeks and the product is not therefore very persistent;

imidacloprid-based products, such as the products Advantage® Chat and Advantage® Chien, sold in France by Bayer Pharma Division Sante Animale [Animal Health Division]. According to the producer's data, the fleas are killed within 24 hours after application of the treatment and the period of protection against further infestations is 4 weeks. Thus, the rapidity of action and the persistence of these products are not entirely satisfactory;

the combination of permethrin and imidacloprid sold under the name Advantix® by the company Bayer or else the combination of permethrin and pyriproxyfen sold under the name Duowin® Contact by the company Virbac, which both have the major drawback of being intended only for dogs since they are very toxic in cats.

Other documents envision the topical administration of products against external parasites.

In particular, patent application EP 0 616 494, cited above, mentions the topical route among various routes of administration of 1-N-(halo-3-pyridylmethyl)-N-methylamino-1-alkylamino-2-nitroethylene derivatives; however, it is not the pathway described as being the most advantageous.

Patent application DE 198 07 633 proposes a composition for limiting the dermal development of parasitic insects in animals; this water-based composition also comprises a nicotinic acetylcholine receptor agonist or antagonist and a solvent chosen from cyclic carbonates and lactones.

Patent application EP 0 976 328 describes an agent for combating ectoparasites in animals, comprising a neonicotinoid and a solvent chosen from a glycol ether or a glycol monoalkyl ether.

Patent application WO 2004/064522 describes topical formulations combining (i) a type I or type II pyrethroid, a pyrethroid with no ester function or a natural pyrethroid, with (ii) a compound chosen from neonicotinoids, nithiazine and spinosyns.

Patent application EP 1 668 984 describes a synergistic combination, for oral or topical administration, composed of a 1-phenylpyrazole derivative, with a pesticide chosen from lactone macrolides, neonicotinoids, insect growth regulators (IGRs), pyrethroids, pyrimidines, organophosphates and amitraz.

Patent application JP 2001/0291535 describes a liquid composition for treating ectoparasites in dogs and cats, comprising a pesticide, an antioxidant and an oily solvent; said pesticide being chosen from pyrethroids, neonicotinoids, phenylpyrazole derivatives, phenylpyrrole derivatives, organophosphates and insect growth regulators.

Patent application JP 2001/0216111 describes a composition for treating the ectoparasites of pets, which is provided in the form of a suspension of a water-insoluble pesticide or of a solution of a water-soluble pesticide. The pesticides can be chosen from pyrethroids, neonicotinoids, phenylpyrazole derivatives, phenylpyrrole derivatives, organophosphates, insect growth regulators and chitin synthesis inhibitors.

However, none of these documents describes the specific use of a 1-N-(halo-3-pyridylmethyl)-N-methylamino-1-alkylamino-2-nitroethylene derivative, such as nitenpyram, topically, nor demonstrates an advantage to the topical use thereof compared with other routes of administration.

Patent application WO 00/29378, the subject of which relates to new antiparasitic compounds, even emphasizes that, when the compounds of general formula (II) which includes nitenpyram are administered topically, the efficacy thereof fades rapidly after administration, thus making it necessary to carry out frequent applications. However, it is impossible, based on this document, to determine the precise conditions for formulation and administration of the compounds of general formula (II) to which these observations correspond.

SUMMARY OF THE INVENTION

Therefore, in order to remedy all the problems encountered with external antiparasitic products, and in particular with the antiflea products currently available on the market, and to provide for a product which makes it possible to effectively prevent and treat flea infestations in domestic animals, both in cats and in dogs, the inventors have developed what forms the subject of the invention. They in particular gave themselves the objective of providing for a product for preventing and treating flea infestations in domestic animals which is compatible with the various life cycles of fleas, and easy to administer, while at the same time having a very rapid and more persistent action than the products currently available on the market.

On this occasion, the applicant discovered, surprisingly, that 1-N-(halo-3-pyridylmethyl)-N-methylamino-1-alkylamino-2-nitroethylene derivatives which were known as active ingredients to be administered preferably systemically, and in particular orally, could advantageously be administered topically and that, in this route of administration, they exhibited a more rapid action and very good persistence; the persistence observed when these derivatives are administered topically is unexpected and much better than the fipronil-based reference products for topical administration, and thus allows the administration of these derivatives to be more spaced out.

The subject of the present invention is thus the use, as active ingredient, of at least one 1-N-(halo-3-pyridylmethyl)-N-methylamino-1-alkylamino-2-nitroethylene derivative of formula (I) below:

(I)

in which:
Hal represents a halogen atom chosen from fluorine, chlorine, bromine and iodine,
$R_1$ and $R_2$, which may be identical or different, represent a hydrogen atom, a $C_1$-$C_6$ alkyl radical or a $C_3$-$C_7$ cycloalkyl radical,
$R_3$ represents a hydrogen atom or a $C_1$-$C_6$ alkyl radical, and of at least one pharmaceutically acceptable carrier, for preparing a pharmaceutical composition for topical administration in the prevention and/or treatment of infestations with external parasites, in particular fleas, in domestic animals, which use is characterized in that said composition is intended to be applied at least every 2 weeks, preferably at least every 4 weeks, and more preferably at least every 7 weeks.

DETAILED DESCRIPTION OF THE INVENTION

When the composition is intended to be applied at least every 2 weeks (14 days), it is understood that it will make it possible to be effective for at least 14 days and that it will not be necessary to retreat the animal during this period of time.
According to one particular variant embodiment of the use according to the invention, said pharmaceutical composition is intended to be applied every 2 to 12 weeks, every 4 to 10 weeks or every 7 to 8 weeks.

According to one particularly preferred variant, said composition is a liquid composition comprising at least one pharmaceutically acceptable liquid carrier.
According to the invention, said pharmaceutical composition is in particular intended to be administered to cats or to dogs.
According to this use, the compound(s) of formula (I) is (are) preferably chosen from the compounds in which the halogen atom denoted by Hal is located in position 6 of the pyridyl ring and preferably denotes a chlorine atom.
According to one particularly preferred embodiment of the invention, the compound(s) of formula (I) is (are) chosen from those in which $R_1$ represents a hydrogen atom, a $C_1$-$C_3$ alkyl radical or a $C_3$-$C_6$ cycloalkyl radical, and even more preferably from those in which $R_1$ represents a hydrogen atom or an ethyl or cyclopropyl radical, it being understood that, among the latter designations, the ethyl designation is most particularly preferred.
According to this embodiment of the invention, the compound(s) of formula (I) is (are) preferably chosen from those in which $R_2$ represents a $C_1$-$C_3$ alkyl radical or a cyclopropyl radical; the designation methyl for $R_2$ being particularly preferred.
Moreover, the compound(s) of formula (I) is (are) also preferably chosen from those in which $R_3$ represents a hydrogen atom.
According to one particularly preferred embodiment of the invention, the pharmaceutical composition comprises, as particular compound of formula (I), (E)-N-(6-chloro-3-pyridyl-methyl)-N-ethyl-N'-methyl-2-nitrovinylidenediamine, also called nitenpyram.
Within the pharmaceutical composition used in accordance with the invention, the compound(s) of formula (I) preferably represent(s) from 0.1% to 90% by weight relative to the total weight of the composition, more preferably from 1% to 50% by weight of the total weight of the composition, more preferably from 5% to 20% by weight of the total weight of the composition, and even more preferably approximately 10% by weight of the total weight of the composition. It should, however, be understood that these percentages can be modulated according to the requirements of the formulation with regard to the effective doses of the active ingredient under consideration.
According to the invention, the compound(s) of formula (I) is (are) generally administered to the animal in a unit dose of between approximately 0.01 and approximately 800 mg/kg of body weight, more preferably between approximately 0.1 and 200 mg/kg of body weight, and even more preferably between approximately 0.5 and 30 mg/kg of body weight.
For the purpose of the present invention, the term "pharmaceutically acceptable liquid carrier" is intended to mean any liquid excipient, the use of which is compatible with topical administration to domestic animals, and in particular to cats and dogs.
According to the invention, the pharmaceutically acceptable liquid carrier is preferably a solvent, such as a solvent chosen from water, an alcohol, a glycol ether or a glycol monoalkyl ether, and mixtures thereof. Preferably, the alcohol is chosen from ethanol and benzyl alcohol; the glycol ether is chosen from dipropylene glycol n-butyl ether and propylene glycol; and the glycol monoalkyl ether is chosen from propylene glycol monomethyl ether, ethylene glycol monomethyl ether, ethylene glycol monoethyl ether and diethylene glycol monoethyl ether.
Other solvents can be used as pharmaceutically acceptable liquid carrier without any significant difference having been observed in terms of efficiency of the composition. These solvents can be chosen from polar or nonpolar (apolar) organic solvents, such as dimethyl sulfoxide (DMSO), propylene carbonate, N-methyl-2-pyrrolidone (NMP), isopropylene glycerol and N-octylpyrrolidone. The pharmaceutical composition may also comprise fatty substances, such as fatty acids or fatty acid esters, as solvents/cosolvents. As fatty substances, mention may in particular be made of oleic acid or else isopropyl myristate.

The pharmaceutical composition used in accordance with the invention may also contain one or more excipients having various properties and which may, for example, be chosen from surfactants such as polysorbates, in particular polysorbate 80, or fatty acid and fatty alcohol esters, in particular cetostearyl octanoate, thickeners, pH regulators, colorants, aromas or fragrances, antioxidants, among which mention may be made, by way of nonlimiting example, of butylhydroxyanisole, butylhydroxytoluene, propyl gallate, ascorbyl palmitate, or extracts of rosemary, and mixtures thereof. In particular, some excipients may contribute to further improving the desired effect of persistence of the activity against ectoparasites. Crystallization inhibitors and also film-forming agents such as polyvinylpyrrolidones and copolymers thereof are constituents of choice for this purpose.

According to one advantageous embodiment of the invention, in addition to the compound(s) of formula (I), the pharmaceutical composition also comprises one or more additional active compounds chosen from ingredients that are active with respect to the prevention and/or treatment of fleas and/or ticks and/or sandflies and ectoparasites in general in domestic animals.

Among these additional active ingredients, mention may more particularly be made of phenylpyrazole derivatives such as, for example, fipronil, pyrethrinoids such as, for example, flumethrin and permethrin, chloronicotinyls such as, for example, imidacloprid, and insect growth regulators such as pyriproxyfen or alternatively (S)-methoprene. Such combinations of active agents within the composition may be of use for the purpose of improving the efficiency of each active agent taken individually or of broadening the spectrum of action of the composition in order, for example, for the composition to be equally effective against tick infestations and/or sandfly infestations, or else for the purpose of reducing the doses of the individual active agents in order to combat, for example, the possible negative effects thereof on the environment, or to combat resistance phenomena, while at the same time maintaining satisfactory insecticidal efficiency.

For implementing the use according to the invention, it is, moreover, advantageous to combine the compounds of general formula (I) with other types of additional active compounds chosen from ingredients that are active with respect to the prevention and/or treatment of endoparasites in general in domestic animals, such as praziquantel or avermectins and derivatives thereof, for instance ivermectin, abamectin or doramectin, or else milbemycins such as milbemycin oxime or moxidectin, in order to prevent and/or treat internal parasitoses at the same time as external infestations.

When the additional active agent must cross the skin barrier in order to exert a systemic activity, the choice thereof will condition the choice of the formulation excipients. This formulation should, moreover, exhibit satisfactory stability.

According to one particularly advantageous embodiment, the liquid pharmaceutical composition contains a combination of (E)-N-(6-chloro-3-pyridylmethyl)-N-ethyl-N'-methyl-2-nitrovinylidenediamine (nitenpyram) and 5-amino-1-[2,6-dichloro-4-(trifluoromethyl)phenyl]-4-(trifluoromethylsulfinyl)-1H-pyrazole-3-carbonitrile (fipronil). The inventors have in fact demonstrated that the topical administration of nitenpyram alone already exhibits greater efficiency than fipronil, which is the product currently considered to be the most effective on the market, but that the efficiency of nitenpyram can be further improved when it is administered concomitantly with fipronil.

The nitenpyram/fipronil weight ratio is preferably between 1/10 and 10/1. In one particularly preferred embodiment of the invention, this weight ratio is 1/1.

A pharmaceutical composition that is particularly preferred according to the invention comprises (by weight relative to the total weight of said composition):

1% to 20% of nitenpyram,

1% to 20% of fipronil,

98% to 60% of one or more excipients as defined above.

According to another advantageous embodiment, the pharmaceutical composition contains a combination of (E)-N-(6-chloro-3-pyridylmethyl)-N-ethyl-N'-methyl-2-nitrovinylidenediamine (nitenpyram) and N,N'-[(methylimino)dimethylidyne]bis(2,4-xylidine) (amitraz).

According to another advantageous embodiment, the pharmaceutical composition contains a combination of nitenpyram, moxidectin and praziquantel.

According to yet another variant, the pharmaceutical composition contains a combination of (E)-N-(6-chloro-3-pyridylmethyl)-N-ethyl-N'-methyl-2-nitrovinylidenediamine (nitenpyram) and 3-phenoxybenzyl(1RS)-cis,trans-3-(2,2-dichlorovinyl)-2,2-dimethylcyclo-propanecarboxylate (permethrin). The composition may then be in the form of a suspension or a solution for topical application or else in the form of a device for controlled release of the active ingredients on the skin and the hairs of the domestic animal, such as a collar for example.

The liquid pharmaceutical composition used in accordance with the invention can be readily prepared by simple dilution or dissolution of the compound(s) of formula (I) and optionally of the additional active ingredient(s) in the solvent(s) used.

After it has been prepared, the liquid pharmaceutical composition is preferably packaged in single-dose pipettes.

According to the invention, the liquid pharmaceutical composition is preferably administered by direct application to the skin of the animal, at the level of the shoulder blades or on a dorsal line from the base of the tail up to the neck.

According to another of the subjects thereof, the present invention relates to a method for preventing and/or treating ectoparasite infestations, in particular flea infestations, of domestic animals, in particular dogs and cats. The method then consists essentially of the topical administration of derivatives of formula (I) at least every 2 weeks.

In addition to the above arrangements, the invention also comprises other arrangements which will emerge from the description that follows, which refers to examples demonstrating the efficiency of nitenpyram, when it is administered alone or in combination with fipronil by topical application, and also to FIGS. 1 to 5 which represent the comparative efficiency (as %) of various antiflea treatments (nitenpyram alone at 10%: solid squares; nitenpyram at 10%+fipronil at 10%: solid diamonds; fipronil alone at 10%: solid triangles) in cats as a function of time (in days).

It should, however, be clearly understood that these examples are given only by way of illustration of the subject of the invention, of which they in no way constitute a limitation.

Example 1

Study of the Rapidity of Action of a Nitenpyram-Based Composition Administered Topically In this example, a comparative study of the efficacy of nitenpyram (rapidity of action) administered topically, alone or in combination with fipronil, compared with fipronil administered alone, against cat fleas, was carried out.

1) Materials and Methods a) Type of Study

It is a randomized, blind, controlled efficacy study carried out in parallel on 4 groups of six cats, according to the recommendations of the guidelines of the Committee for Veterinary Medicinal Products (CVMP): "*Guidelines for the testing and evaluation of the efficacy of antiparasitic substances for the treatment and prevention of tick and flea infestations in dogs and cats*", EMEA/CVMP/005/00-FINAL-Rev.1.

b) Animals Used and Maintenance Conditions

The cats used in this study were male or female, adult domestic cats more than 6 months old, of mixed breeds, but mainly of short-hair European breed, weighing between 2 and 5 kg. Before the beginning of the study, it was verified that all the cats were in good health, that they were not infested with fleas and that the females were not pregnant. All the cats were wormed and acclimatized to the living conditions for at least 7 days before the study was begun.

It was also verified that the cats had not received any topical treatment against fleas during the 12 weeks preceding the beginning of the study.

During the acclimatization period and throughout the duration of the study, the cats were kept inside in an air-conditioned room, each cat being confined in individual stainless steel cages with the dimensions of 70×60×75 cm, without litter. The identification number, the group No. and the type of composition administered were noted on each cage. The temperature of the room was kept at approximately 20° C.±4° C. The cats were subjected to alternating periods of 12 hours of light and 12 hours of darkness.

The animals were fed once a day with commercial dry catfood, sold under the trademark Iams® Adult, according to the manufacturer's recommendations, and they had unlimited fresh drinking water.

c) Compositions Tested

The following compositions were prepared, the formulation thereof being reported in Table I hereinafter:

TABLE 1

| Ingredients | COMPOSITIONS | | |
|---|---|---|---|
| | A | B | C[a] |
| Nitenpyram (% w/v) | 10 | 10 | — |
| Fipronil (% w/v) | 10 | — | 10 |
| Diethylene glycol monoethyl ether | qs | qs | — |
| Excipients of the product Frontline ® Top-Spot | — | — | qs |

[a]Composition C corresponds to the commercial product sold under the name Frontline ® Top-Spot by the company Mérial. It was used as supplied by the manufacturer.

d) Treatments

Group 1: treatment with composition A in a proportion of 0.5 ml per cat,

Group 2: treatment with composition B in a proportion of 0.5 ml per cat,

Group 3: treatment with composition C in a proportion of 0.5 ml per cat,

Group 4: negative control: no treatment.

The treatment was applied topically, between the shoulder blades of the cats, in a single application at the beginning of the study (D=0).

e) Flea Infestations/Measurement of Treatment Efficacy 6 days before the beginning of the study (D=−6), all the cats were infested with approximately 100 laboratory fleas, strain *Ctenocephalides felis*, of male or female gender. The fleas were then counted on the day before the treatment (D=−1) and then at different times after application of the treatment (1, 4, 12 and 24 hours after treatment).

To do this, all the fleas present on an animal are harvested by combing the cat and then counting after combing. The number of live fleas is thus determined. After each count, the live fleas are put back onto the cat.

At each count, the efficacy of the treatment was calculated according to the following equation:

$$\% \text{ efficacy} = 100 \times (NP_v C - NP_v T)/NP_v C$$

in which:

$NP_v C$ is the geometric mean of the number of live fleas counted on the cats of group 4 (control);

$NP_v T$ is the geometric mean of the number of live fleas counted on the cats of a group having received a treatment (groups 1, 2 or 3).

2) Results

Figure 1:
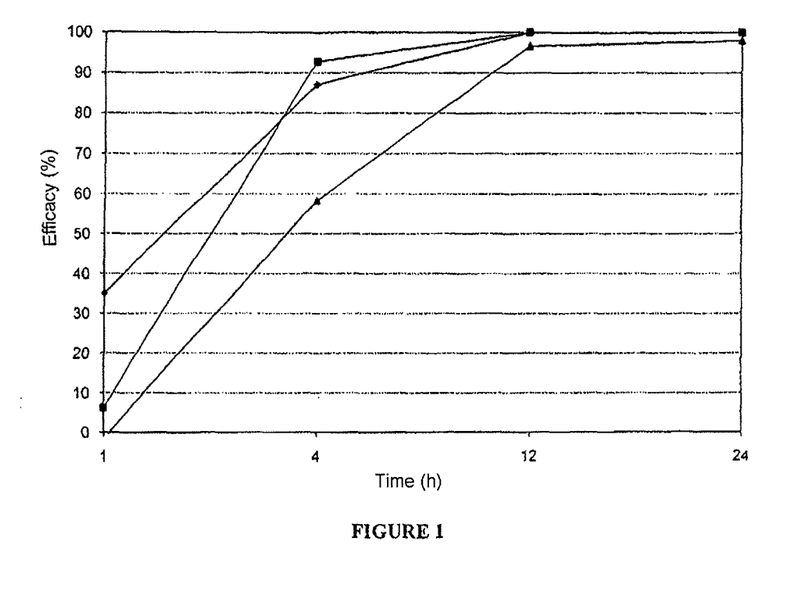
FIG. 1 is a chart showing % efficacy of three different compositions containing nitenpyram, fipronil and a combination thereof as a function of time in the treatment of flea infestations.

The results obtained are represented on the attached FIG. 1, on which the percentage efficacy of each treatment is as a function of time (in hours).

On this figure, the solid diamonds correspond to the results of group 1 (treatment with composition A containing 10% of nitenpyram and 10% of fipronil), the solid squares correspond to the results of group 2 (treatment with composition B containing 10% of nitenpyram) and the solid triangles correspond to the results of group 3 (treatment with composition C containing 10% of fipronil).

These results show that the topical administration of nitenpyram has a lethal effect on the cat fleas. These results also show that compositions A and B in accordance with the present invention, i.e. comprising nitenpyram, have a more rapid action than prior art composition C based on fipronil. This superiority is even more marked in the case of composition A, which contains a combination of nitenpyram and fipronil.

Example 2

Preliminary Study of the Efficacy Over Time of a Nitenpyram-Based Composition Against Fleas in Cats In this example, the duration of efficacy of a topical formulation containing 20% by weight of nitenpyram, against flea infestations in cats, was studied.

This study was carried out on two cats of European breed weighing 5.5 and 3.8 kg, respectively. Throughout the duration of the experiment, the cats were placed in cages and fed according to the protocol indicated above in Example 1.

One day before the administration of the treatment, the cats were infested with a known amount of fleas of race identical to that used in Example 1 above.

Each cat then received, between the shoulder blades, a dose of 0.5 ml of topical formulation having the following composition:

nitenpyram 20 g diethylene glycol monoethyl ether qs 100 ml

The number of fleas still alive 4 hours after the administration of the composition was then counted (D=0).

The cats were again infested with a known amount of fleas 7 days (D=7), 14 days (D=14), 21 days (D=21), 35 days (D=35) and 42 days (D=42) after administration of the treatment.

A count of the fleas still alive was then performed at 24 hours after each of these new infestations (D=8; D=15; D=22; D=36 and D=43).

The percentage efficacy of the treatment was then calculated by applying the following formula:

% efficacy=100×(NPinit.−NPV)/NPinit.

in which:
NPinit. corresponds to the initial number of fleas before administration of the treatment,
NPV: corresponds to the number of fleas still alive at D=0, D=8, D=15, D=22, D=36 or D=43.

The mean results obtained are reported in Table II hereinafter:

TABLE II

|  | D = 0 | D = 8 | D = 15 | D = 21 | D = 36 | D = 43 |
|---|---|---|---|---|---|---|
| Number of fleas alive (mean of two cats) | 0 | 0 | 0 | 0 | 0 | 2.9 |
| Efficacy (%) | 100 | 100 | 100 | 100 | 100 | 92.8 |

These results demonstrate that the single application of a nitenpyram-based topical composition has a sustained efficacy over time, since 35 days after the administration of the insecticidal composition, 100% efficacy is still observed (persistent effect).

Example 3

Supplementary Study of the Efficacy Over Time of a Nitenpyram-Based Composition Against Fleas in Cats In this example, a comparative study of the efficacy, over time, of nitenpyram administered topically, alone or in combination with fipronil, compared with fipronil administered alone, against cat fleas, was carried out. It is the continuation of the study of example 1 using compositions A, B and C.

1) Measurement of Treatment Efficacy

At a regular interval after the first administration (D=0), all the cats were infested with approximately 100 laboratory fleas, strain *Ctenocephalides felis*, of male or female gender. The re-infestations were thus carried out at D=7, D=14, D=21, D=28, D=35, D=42, D=49, D=56 and D=63. The fleas were then counted various times after application of the treatment (at 2, 4 and 12 hours after re-infestation at D=7, D=14, D=21 and D=28; at 4, 8 and 12 hours after re-infestation at D=35 and D=42; at 12, 24 and 48 hours after re-infestation at D=49; at 24 and 48 hours after re-infestation at D=56 and, finally, at 48 hours after re-infestation at D=63).

To do this, all the fleas present on an animal were harvested by combing the cat, and then counted after combing. The number of live fleas is thus determined. After each count, the live fleas are put back on the cat.

At each count, the efficacy of the treatment was calculated according to the following equation:

% efficacy=100×(NP$_v$C−NP$_v$T)/NP$_v$C in which:
NP$_v$C is the geometric mean of the number of live fleas counted on the cats of group 4 (control);

NP$_v$T is the geometric mean of the number of live fleas counted on the cats of a group having received a treatment (groups 1, 2 or 3).

2) Results

The results obtained are represented in Table III hereinafter, which represents, for each group, the percentage of dead fleas counted at various times after infestation:

TABLE III

| Days of infestation | Time (hours after infestation) | GROUP 1 (10% fipronil + 10% nitenpyram) | GROUP 2 (10% nitenpyram) | GROUP 3 (10% fipronil) |
|---|---|---|---|---|
| D = 7 | 2 | 68.6 | 82.1 | 51.0 |
|  | 4 | 99.2 | 99.8 | 96.8 |
|  | 12 | 100.0 | 100.0 | 100.0 |
| D = 14 | 2 | 54.1 | 58.1 | 50.2 |
|  | 4 | 95.8 | 98.4 | 96.2 |
|  | 12 | 100.0 | 100.0 | 100.0 |
| D = 21 | 2 | 46.9 | 66.9 | 21.7 |
|  | 4 | 93.1 | 97.5 | 87.5 |
|  | 12 | 99.4 | 100.0 | 100.0 |
| D = 28 | 2 | 27.4 | 32.8 | 18.6 |
|  | 4 | 71.4 | 85.1 | 80.0 |
|  | 12 | 99.4 | 99.7 | 100.0 |
| D = 35 | 4 | 61.8 | 55.0 | 34.4 |
|  | 8 | 89.9 | 95.4 | 83.4 |
|  | 12 | 96.5 | 99.4 | 93.2 |
| D = 42 | 8 | 45.6 | 48.1 | 36.9 |
|  | 12 | 83.3 | 93.1 | 78.2 |
|  | 24 | 99.3 | 100.0 | 91.7 |
| D = 49 | 12 | 65.0 | 65.5 | 45.7 |
|  | 24 | 95.2 | 96.6 | 84.5 |
|  | 48 | 100.0 | 100.0 | 89.6 |
| D = 56 | 24 | 80.7 | 72.6 | 54.1 |
|  | 48 | 98.2 | 94.4 | 69.9 |
| D = 61 | 48 | 70.0 | 69.6 | — |

These results are also reported on the attached FIGS. 2 to 5, which make it possible to compare both the rapidity with which the various treatments tested are effective and the persistence of these treatments applied topically. The accepted standard of 95% in terms of insecticidal efficacy is used here: 95% of the fleas should be killed in order for the veterinary treatment to be considered effective.

Figure 2:
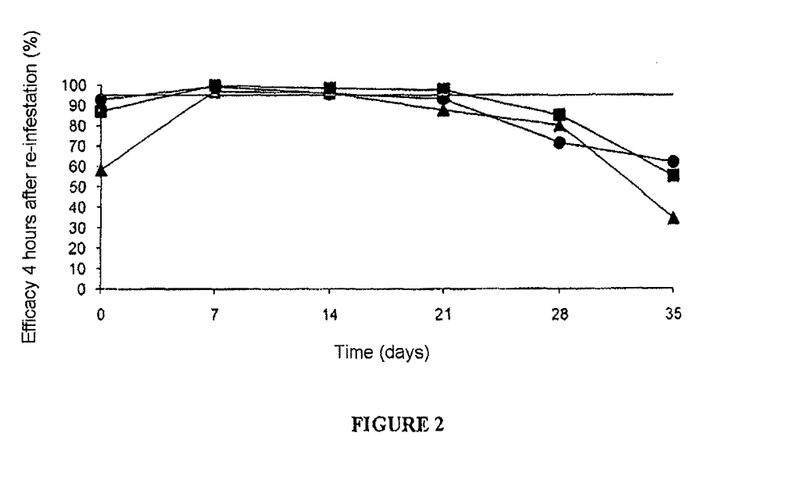
FIG. 2 represents the comparative efficiency of the three compositions of FIG. 1, measured by flea count, as a function of time after 4 hours.

FIG. 2 represents the comparative efficacy of the three compositions A, B and C (as %), measured by flea count, as a function of time, i.e. 4 hours after re-infestation on days D=7; D=14; D=21; D=28; D=35; D=42 and D=49.

Figure 3:
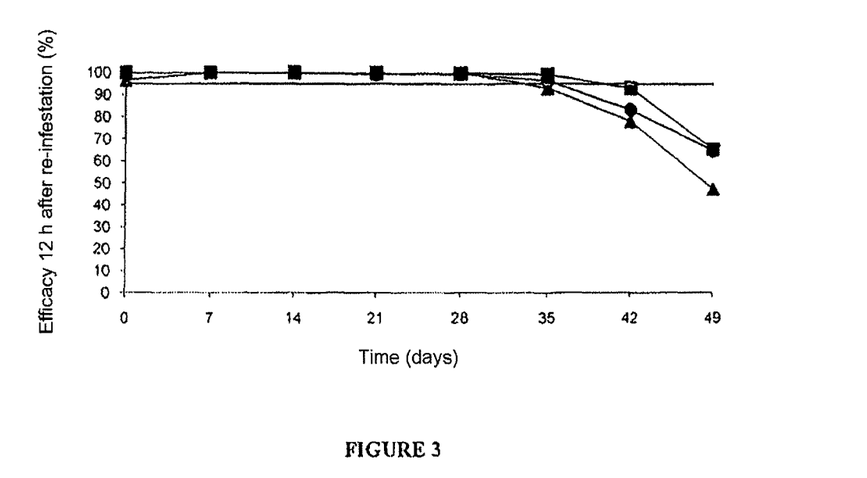
FIG. 3 represents the comparative efficiency of the three compositions of FIG. 1, measured by flea count, as a function of time after 12 hours.

FIG. 3 represents the comparative efficacy of the three compositions A, B and C (as %), measured by flea count, as a function of time, i.e. 12 hours after re-infestation on days D=7; D=14; D=21; D=28; D=35; D=42 and D=49.

Figure 4:
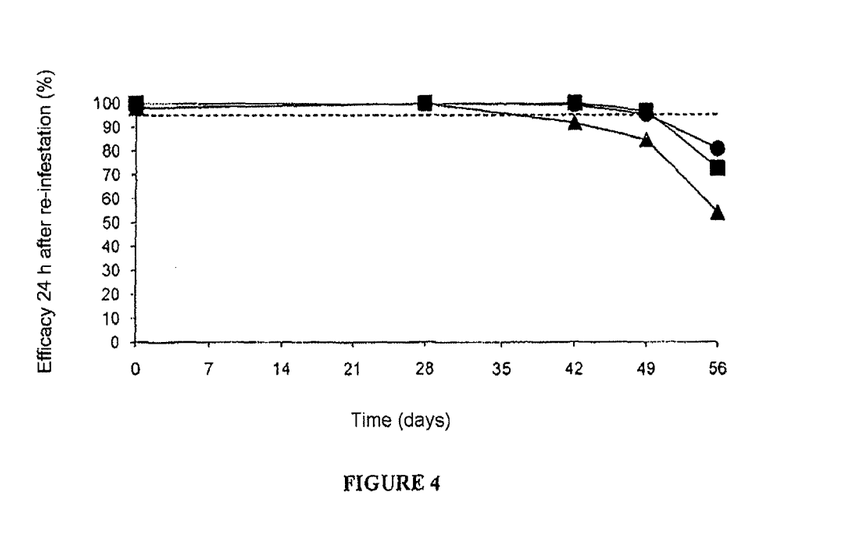
FIG. 4 represents the comparative efficiency of the three compositions of FIG. 1, measured by flea count, as a function of time after 24 hours.

FIG. 4 represents the comparative efficacy of the three compositions A, B and C (as %), measured by flea count, as a function of time, i.e. 24 hours after re-infestation on days D=7; D=14; D=21; D=28; D=35; D=42; D=49 and D=56.

Figure 5:
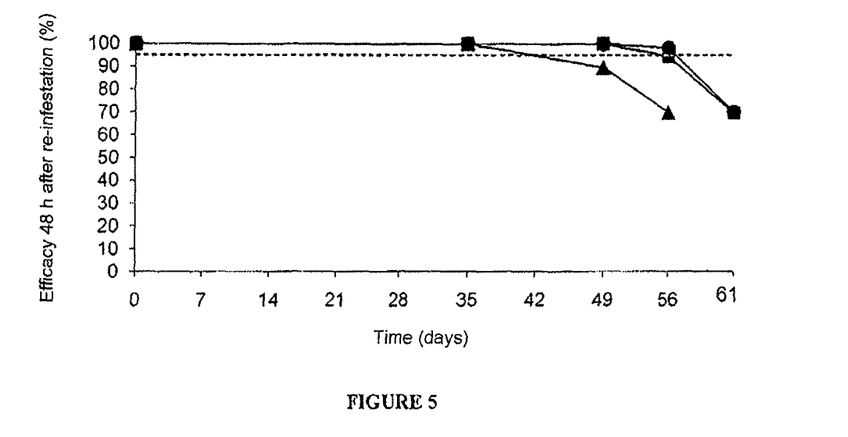
FIG. 5 represents the comparative efficiency of the three compositions of FIG. 1, measured by flea count, as a function of time after 48 hours.

FIG. 5 represents the comparative efficacy of the three compositions A, B and C (as %), measured by flea count, as a function of time, i.e. 48 hours after re-infestation on days D=7; D=14; D=21; D=28; D=35; D=42; D=49; D=56 and D=61.

On all these figures, the solid squares correspond to the results of group 1 (treatment with composition A containing 10% of nitenpyram and 10% of fipronil), the solid circles correspond to the results of group 2 (treatment with composition B containing 10% of nitenpyram) and the solid triangles correspond to the results of group 3 (treatment with composition C containing 10% of fipronil).

These results show that the residual protection period, calculated in number of weeks, during which the efficacy of the compositions against fleas is greater than or equal to 95% is:

four weeks for group 3 (treatment with composition C containing 10% of fipronil alone) when it is evaluated up to 12 hours after re-infestation;

seven weeks for group 2 (treatment with composition B containing 10% nitenpyram alone) when it is evaluated up to 48 hours after re-infestation; and eight weeks for group 1 (treatment with composition A containing 10% of nitenpyram and 10% of fipronil) when it is evaluated 48 hours after re-infestation.

These results show that the topical administration of nitenpyram has a rapid and sustained lethal effect on cat fleas. These results also show that compositions A and B in accordance with the present invention, i.e. comprising nitenpyram, have a more rapid action than prior art composition C based on fipronil alone. This superiority is even more marked in the case of composition A, which contains a combination of nitenpyram and fipronil.

These results confirm, moreover, that the single application of a nitenpyram-based topical composition has a sustained efficacy over time, since 57 days after administration of the insecticidal composition, an efficacy against fleas of greater than 95% is still observed. The persistent effect of the nitenpyram-based composition for topical application is thus clearly demonstrated.

Example 4

Comparative Study of the Pharmacokinetics of Nitenpyram Administered Orally and Topically In this example, a comparative study of the pharmacokinetics of nitenpyram administered topically and orally to cats was carried out.

The cats used in this study were prepared under the same conditions as those described in example 1.

It was verified, beforehand, that no trace of nitenpyram was detected in the plasma of the cats.

1) Materials and Methods

The pharmacokinetic profile of nitenpyram was studied according to the following methods.

Ten young adult cats weighing between 2 and 6 kg are divided up into two groups:
- a first group of 5 cats (female) received a single topical administration on the back between the shoulder blades at the beginning of the study; the topical composition is a solution containing 10% of nitenpyram (100 mg of nitenpyram per ml) and the amount administered is 0.5 ml per cat.
- a second group (4 females and one male) received a single oral administration of the commercial product Capstar® given at the beginning of the study. The Capstar® product is a tablet comprising 11.4 mg of nitenpyram.

Blood samples were taken regularly, and centrifuged at 3000 rpm for 10 minutes at 4° C., the pellet is removed and the plasma is recovered for analysis.

The plasma concentration of nitenpyram is determined by the UPLC-MS/MS (Ultra-Performance Liquid Chromatography coupled to tandem mass spectrometry) method on an Acquity BEH $C_{18}$ column and a Waters Quattro Premier XE mass spectrophotometer.

2) Results

It is noted that the topical administration of nitenpyram is well tolerated locally. Similarly, the oral administration of nitenpyram is well tolerated.

The pharmacokinetic parameters determined in the context of the present study are summarized in Table IV hereinafter.

TABLE IV

| | Topical administration | Oral administration |
|---|---|---|
| Cmax: maximum amount of nitenpyram in the plasma (ng · ml$^{-1}$) | 1291 | 5898 |
| Tmax: time at which the maximum concentration of nitenpyram in the plasma is observed (h) | 15.0 | 1.3 |
| AUCtot: area under the curve of the nitenpyram concentration over time determined between t0 and the final measurement (ng · h · ml$^{-1}$) | 86361 | 76773 |
| Thalf: half-life time (h) | 69.1 | 9.8 |

It is observed that, when nitenpyram is administered topically, the maximum plasma concentration of active agent (Cmax) is reached later than with oral administration: the Tmax of nitenpyram for topical administration being 15.0 hours against 1.3 hours for oral administration.

Although the maximum plasma concentration of nitenpyram is lower with topical administration (1291 ng·ml$^{-1}$) than that measured with oral administration (more than 5800 ng·ml$^{-1}$), it is observed that the AUCtot value, which represents the total amount of active agent present in the plasma throughout the experiment, is higher in the case of topical administration. In addition, the half-life time of nitenpyram (Thalf which corresponds to half the time necessary for elimination of the active agent) administered topically is more than 7 times longer (69.1 hours) than that of nitenpyram administered orally (9.8 hours).

3) Conclusion

These results show that topical administration of nitenpyram results in passage of the active agent into the blood of the animals. This passage occurs more slowly and over a longer period of time than when the nitenpyram is administered orally; this makes it possible to partly explain why nitenpyram administered topically has a sustained efficacy over time.

Thus, topical administration of nitenpyram offers the advantage of providing:
- an immediate antiflea effect by contact; this immediate effect is necessary in order to prevent any flea bite and reproduction of the flea. It is noted that the contact efficacy is sustained over time (see examples 2 and 3); and
- a systemic effect sustained over time (poisoning of the fleas by the blood) compared with that obtained when nitenpyram is administered orally.

The persistent contact effect and the sustained systemic effect allow less regular administration of the composition and a dosage that is more suited to what consumers want.

Example 5

Topical Formulations

Composition 1

| | |
|---|---|
| Moxidectin | 2.5% |
| Praziquantel | 8.5% |
| Nitenpyram | 10% |
| BHA | 0.094% |
| BHT | 0.047% |
| Benzyl alcohol | 25% |
| DMSO | 20% |
| Polysorbate | 805% |
| PVP K17 | 5% |
| Solketal (or isopropylidene glycerol) | qs. |

Composition 2

| | |
|---|---|
| Moxidectin | 2.5% |
| Praziquantel | 8.5% |
| Nitenpyram | 10% |
| BHA | 0.094% |
| BHT | 0.047% |
| Benzyl alcohol | 25% |
| NMP | 20% |
| Polysorbate 80 | 5% |
| PVP K17 | 5% |
| Oleic acid | 5% |
| Propylene carbonate | qs. |

Composition 3

| | |
|---|---|
| Moxidectin | 2.5% |
| Praziquantel | 8.5% |
| Nitenpyram | 10% |
| BHA | 0.094% |
| BHT | 0.047% |
| Benzyl alcohol | 25% |
| Isopropyl myristate | 10% |
| Polysorbate 80 | 5% |
| PVP K17 | 5% |
| Solketal | qs. |

Composition 4

| | |
|---|---|
| Moxidectin | 2.5% |
| Nitenpyram | 5% |
| BHA | 0.094% |
| BHT | 0.047% |
| Benzyl alcohol | 25% |
| NMP | 20% |
| Polysorbate 80 | 5% |
| PVP K17 | 5% |
| Oleic acid | 5% |
| Propylene carbonate | qs. |

Composition 5

| | |
|---|---|
| Nitenpyram | 5% |
| BHA | 0.094% |
| BHT | 0.047% |
| Benzyl alcohol | 25% |
| NMP | 20% |
| Polysorbate 80 | 5% |
| PVP K17 | 5% |
| Oleic acid | 5% |
| Propylene carbonate | qs. |

Composition 6

| | |
|---|---|
| Praziquantel | 8.5% |
| Nitenpyram | 10% |
| BHA | 0.094% |
| BHT | 0.047% |
| Benzyl alcohol | 25% |
| NMP | 20% |
| Polysorbate 80 | 5% |
| PVP K17 | 5% |
| Oleic acid | 5% |
| Propylene carbonate | qs. |

Composition 7

| | |
|---|---|
| Nitenpyram | 5% |
| BHA | 0.094% |
| BHT | 0.047% |
| Benzyl alcohol | 25% |
| NMP | 20% |
| Polysorbate 80 | 5% |
| PVP K17 | 5% |
| Oleic acid | 5% |
| Propylene carbonate | qs. |

Composition 8

| | |
|---|---|
| Moxidectin | 2.5% |
| Praziquantel | 8.5% |
| Nitenpyram | 10% |
| Pyriproxifen | 10% |
| BHA | 0.094% |
| BHT | 0.047% |
| Benzyl alcohol | 25% |
| NMP | 20% |
| Polysorbate 80 | 5% |
| PVP K17 | 2.5% |
| Propylene carbonate | qs. |

Composition 9

| | |
|---|---|
| Moxidectin | 2.5% |
| Praziquantel | 8.5% |
| Nitenpyram | 10% |
| Pyriproxifen | 10% |
| BHA | 0.094% |
| BHT | 0.047% |
| Benzyl alcohol | 25% |
| Isopropyl myristate | 8% |
| Polysorbate 80 | 5% |
| PVP K17 | 2.5% |
| Solketal | qs. |

Composition 10

| | |
|---|---|
| Moxidectin | 2.5% |
| Praziquantel | 8.5% |
| Nitenpyram | 2.5% |
| Pyriproxifen | 10% |
| BHA | 0.094% |
| BHT | 0.047% |
| Benzyl alcohol | 25% |
| DMSO | 20% |
| Polysorbate 80 | 5% |
| PVP K17 | 2.5% |
| Solketal | qs. |

Composition 11

| | |
|---|---|
| Nitenpyram | 15% |
| NMP | qs 100 ml |

Composition 12

| | |
|---|---|
| Nitenpyram | 15% |
| N-octylpyrrolidone | qs 100 ml |

Composition 13

| Nitenpyram | 15% |
|---|---|
| DMSO | qs 100 ml |

Composition 14

| Amitraz | 10% |
|---|---|
| Nitenpyram | 15% |
| DMSO | qs 100 ml |

Composition 15

| Amitraz | 10% |
|---|---|
| Nitenpyram | 15% |
| NMP | qs 100 ml |

Composition 16

| Amitraz | 10% |
|---|---|
| Nitenpyram | 15% |
| Isopropyl myristate | 25% |
| NMP | qs 100 ml |

For each of the compositions 1 to 16, satisfactory stability after storage for 4 months at 25° C. was observed; this demonstrates that there is no physical incompatibility of the constituents.

The invention claimed is:

1. A method of killing fleas on a domestic animal comprising topical administering of (E)-N-(6-chloro-3-pyridyl,methyl)-N-ethyl-N'-methyl-2-nitrovinylidenediamine (nitenpyram) to said domestic animal:
   wherein said animal is a cat, and
   wherein said nitenpyram is formulated in a pharmaceutical composition and is applied to said domestic animal at four week or more intervals.

2. The method as claimed in claim 1, wherein said composition is a collar.

3. The method as claimed in claim 1, wherein said composition is a liquid composition comprising at least one pharmaceutically acceptable liquid carrier.

4. The method as claimed in claim 1, wherein, within the pharmaceutical composition, the nitenpyram represent(s) from 5% to 20% by weight relative to the total weight of the composition.

5. The method as claimed in claim 1, wherein the nitenpyram is administered to the animal in a unit dose of between 0.1 and 200 mg/kg of body weight.

6. The method as claimed in claim 3, wherein the pharmaceutically acceptable liquid carrier is a solvent chosen from water, a polar or an apolar organic solvent, an alcohol, a glycol ether and a glycol monoalkyl ether, or mixtures thereof.

7. The method as claimed in claim 6, wherein said solvent is selected in the group consisting of dimethyl sulfoxide, propylene carbonate, N-methyl-2-pyrrolidone, isopropylene glycerol, N-octylpyrrolidone, ethanol, benzyl alcohol, propylene glycol monomethyl ether, dipropylene glycol n-butyl ether, ethylene glycol monomethyl ether, ethylene glycol monoethyl ether, diethylene glycol monoethyl ether and propylene glycol, and mixtures thereof.

8. The method as claimed in claim 6, wherein the pharmaceutical composition also contains one or more excipients chosen from surfactants, thickeners, pH regulators, colorants, crystallization inhibitors, film-forming agents and antioxidants, and mixtures thereof.

9. The method as claimed in claim 1, wherein the pharmaceutical composition further comprises one or more ectoparasiticidal agents.

10. The method as claimed in claim 9, wherein the ectoparasiticidal agent(s) is (are) selected in the group consisting of phenylpyrazole derivatives, pyrethrinoids, chloronicotinyls, insect growth regulators and amitraz.

11. The method as claimed in claim 10, wherein the pharmaceutical composition contains a combination of (E)-N-(6-chloro-3-pyridylmethyl)-N-ethyl-N'-methyl-2-nitrovinylidenediamine (nitenpyram) and 5-amino-1-[2,6-dichloro-4-(trifluoromethyl)phenyl]-4-(trifluoromethylsulfinyl)-1H-pyrazole-3-carbonitrile (fipronil).

12. The method as claimed in claim 1, wherein the pharmaceutical composition further comprises one or more endoparasiticidal agent.

13. The method as claimed in claim 12, wherein said endoparasiticidal agent is selected from the group consisting of praziquantel, avermectins and derivatives thereof and milbemycins.

14. The method as claimed in claim 3, wherein the pharmaceutical composition is packaged in single-dose pipettes.

15. The method as claimed in claim 14, wherein the pharmaceutical composition is administered by direct application to the skin of the animal, at the level of the shoulder blades or on a dorsal line from the base of the tail up to the neck.

16. The method as claimed in claim 1, wherein the animal is free from an external parasite infestation.

17. The method as claimed in claim 1, wherein the animal suffers from an external parasite infestation.

18. The method as claimed in claim 17, wherein the external parasite infestation includes one or more of fleas, ticks, and sandflies.

19. The method as claimed in claim 16, wherein the animal suffers from an endoparasite infestation.

20. The method as claimed in claim 17, wherein the animal also suffers from an endoparasite infestation.

21. The method as claimed in claim 1, wherein said composition is reapplied to said animal every 4 to 10 weeks.

22. A method of killing fleas on a domestic animal comprising topical administering of (E)-N-(6-chloro-3-pyridylmethyl)-N-ethyl-N'-methyl-2-nitrovinylidenediamine (nitenpyram) to said domestic animal
   wherein said animal is a cat,
   wherein said nitenpyram is applied to said domestic animal at four week or more intervals, and wherein nitenpyram is formulated in a liquid composition comprising at least one pharmaceutically acceptable liquid carrier selected from the group consisting of dimethyl sulfoxide, propylene carbonate, N-methyl-2-pyrrolidone, isopropylene glycerol, N-octylpyrrolidone, ethanol, benzyl alcohol, propylene glycol monomethyl ether, dipropylene glycol n-butyl ether, ethylene glycol monomethyl ether, ethylene glycol monoethyl ether, diethylene glycol monoethyl ether and propylene glycol, and mixtures thereof.

23. The method of claim 22, wherein said nitenpyram is formulated in a solvent chosen from dimethyl sulfoxide, propylene carbonate, N-methyl-2-pyrrolidone, isopropylene glycerol, N-octylpyrrolidone, ethanol, benzyl alcohol, dipropylene glycol n-butyl ether, propylene glycol, and mixtures thereof.

24. The method of claim 22, wherein said nitenpyram is formulated in a glycol monoalkyl ether solvent.

25. The method of claim 24, wherein the glycol monoalkyl ether solvent is chosen from propylene glycol monomethyl ether, ethylene glycol monomethyl ether, ethylene glycol monoethyl ether, diethylene glycol monoethyl ether, and mixtures thereof.

* * * * *